United States Patent [19]

Baiocchi et al.

[11] 4,264,618

[45] Apr. 28, 1981

[54] BASIC THIO-INDAZOLES

[75] Inventors: Leandro Baiocchi; Bruno Silvestrini, both of Rome, Italy

[73] Assignee: Aziende Chimiche Riunite Angelini Francesco A.C.R.A.F. S.p.A., Rome, Italy

[21] Appl. No.: 102,509

[22] Filed: Dec. 11, 1979

[30] Foreign Application Priority Data

Feb. 19, 1979 [IT] Italy ................ 20305 A/79

[51] Int. Cl.³ ............... A61K 31/415; C07D 231/56
[52] U.S. Cl. ................ 424/273 N; 548/372
[58] Field of Search ............. 548/372; 424/273 N

[56] References Cited

U.S. PATENT DOCUMENTS

| | | | |
|---|---|---|---|
| 3,145,215 | 8/1964 | Kirchner | 424/273 N |
| 3,318,905 | 5/1967 | Palazzo | 548/372 |
| 3,428,634 | 2/1969 | Palazzo | 548/372 |
| 4,182,769 | 1/1980 | Cherkofsky et al. | 424/273 R |

FOREIGN PATENT DOCUMENTS 50-130759  10/1975  Japan .

OTHER PUBLICATIONS

Palazzo et al., J. Med. Chem., 1966, vol. 9, pp. 38–41.
Baiocchi et al., Synthesis 1978, No. 9, pp. 633–648.

*Primary Examiner*—Henry R. Jiles
*Assistant Examiner*—Natalia Harkaway
*Attorney, Agent, or Firm*—Ladas & Parry

[57] ABSTRACT

Compound belonging to the class of 2-benzyl-3-(3-dimethylaminopropylthio)-2H-indazole, its sulfoxide and its sulfone and their pharmacologically acceptable salts, and process for obtaining such compounds having an antiinflammatory action in the common pathological conditions.

8 Claims, No Drawings

BASIC THIO-INDAZOLES

The present invention relates to 2-benzyl-3-(3-dimethylaminopropylthio)-2H-indazole (I) as well as to its sulfoxide (II) and to its sulfone (III):

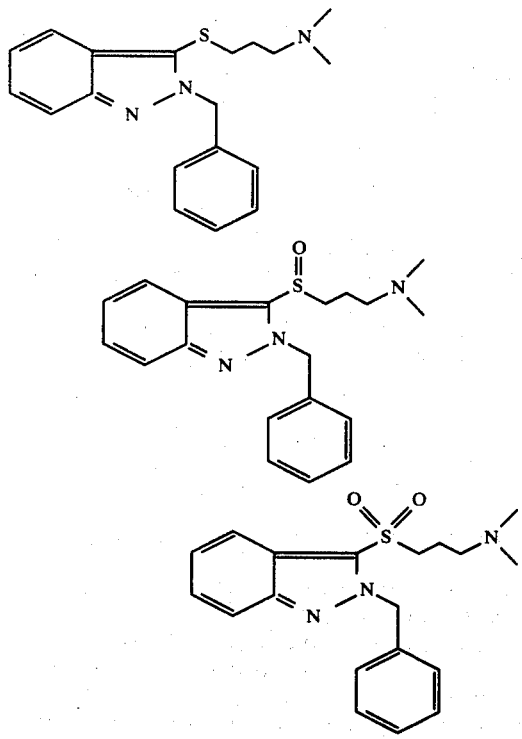

The compounds of the present invention (which will herein after be referred to as "products") belong to the class of the 2-alkyl-3-alkylthio substituted indazoles. This class of compounds has never been previously described; for a complete review of the argument see: L. Baiocchi et al., (Synthesis (9) 1978, 633–648).

The compounds which more closely approximate the products described in the present invention are the 1-alkyl-3-alkyloxy derivatives of the indazole, such as the Benzydamine (G. Palazzo, U.S. Pat. No. 3,318,905, May 9, 1967) and a 1-alkyl-3-alkylthio indazolic derivative (T. Kuroda et al., Japan Kokai 75,130,759; October 16, 1975).

Between the latter and the "products" there exist however substantial differences both on the chemicophysical plane and on the pharmacological plane.

With respect to Benzydamine, for example, compound (I) shows a fluorescence spectrum, in aqueous solution, 100 times less intense (Benzydamine: excitation at 311 nm; emission at 360 nm-Compound (I): excitation at 320 nm; emission at 395 nm).

The pharmacological studies carried out on laboratory animals have shown that the "products" possess antiinflammatory activity, which manifests itself both through the topical and the systemic route, as well as a local anesthetic activity and a disinfectant action which manifest themselves only after topical application. With respect to Benzydamine and to the 1-alkyl-3-alkylthio derivative mentioned before the "products" possess, as will be better described later on, a more favourable ratio between the pharmacological activity and the irritating or toxic effects, which improves and extends the prospectives of use thereof.

On the basis of these results, there can be predicted a therapeutic interest in the common diseases of the inflammatory type, both through the systemic and topical routes. For this latter mode of administration, the local anaesthetic and disinfecting activities constitute a useful complement to the antiinflammatory activity since many inflammatory diseases are accompanied by painful hyperaesthesy and infective phenomena.

The laboratory studies have been conducted utilizing the following tests:

ANTIINFLAMMATORY ACTIVITY

For the systemic route, the antiinflammatory activity has been studied using the method of the plantar edema in the rat, according to the method of Winter et al. (C. A. Winter, E. A. Risely, G. W. Nuss, Proc. Soc. Exp. Biol. Med., 111, 544, 1962). In addition to carrageenin, as phlogogenic agents, there were utilized beer yeast (5%) and a homogenate of connection tissue prepared according to the method of Zucker and Borrelli (M. B. Zucker, J. Borrelli, Proc. Soc. Exp. Biol. Med., 109, 779, 1962). As reference products, there were used acetylsalicylic acid, phenylbutazone, indomethacin and benzydamine. The pharmaceutical products were administered orally, 30 minutes before the injection of the irritating agent. On all three of the irritating agents used, the "products" show a statistically significant antiinflammatory effect starting from the dose of 60 mg/kg p.o. At higher doses the effect of the "products" increases, showing a good dose/effect correlation.

The benzydamine has resulted active at higher doses, with a ratio of 1:2. The indomethacin is active only in the carrageenin test, in good accord with what was previously reported by Winter et al. (1962), while is inactive in the beer yeast and in the tissue homogenate tests. The phenylbutazone and the acetylsalicylic acid are also active against the carrageenin, but not against the beer yeast and the tissue homogenate. The active doses of these two pharmaceutical products are comparable to those of the three "products" here reported.

It can thus be concluded that they present a broader spectrum of anti-inflammatory effects than indomethacin, phenylbutazone and aspirin. They, in addition, with respect to the benzydamine, present the advantage of a more marked antiinflammatory activity.

Topically, the "products" were studied using the same tests described above; they were applied locally in the form of ointment at a 3% and 5% concentration or injected in the paw together with the irritating agent. As reference product there was used the benzydamine, for which there have been reported uses of the local type similar to those predicted for the "products". The latter have effected an anti-inflammatory activity both when applied to the paw in the form of ointment and when injected locally. In this latter case, the active doses are between 0.032 and 0.064 mg/kg. Between the doses active orally and the doses active topically there thus exists a ratio of about 1000:1, which shows that the "products" inhibit the inflammatory processes through local mechanisms.

The benzydamine resulted about two times less active than the products.

LOCAL ANAESTHETIC ACTION

There were utilized the classic test of the local anaesthesia on the eye of the rabbit and the test of the infiltration in the tail of the mouse (C. Bianchi, J. Franceschini, Brit. J. Pharmacol. 9, 290, 1954).

With the first of these two methods there is determined not only the local anaesthetic activity but also the capacity of penetration through the mucous membranes; with the second, on the other hand, there is determined the anaesthetic activity independently from the capacity of penentration through the tissues since the pharmaceutical compound is injected on the inside of said tissues.

As the two values approach each other more and more, this shows a capacity of penetration of the pharmaceutical agent through the tissues. The "products" have resulted active in both tests at the same concentration, i.e., 0.1%.

This result indicates that they possess very good characteristics of penetration through the tissues. The benzydamine shows an activity which is half that of the "products", showing the same behavior as far as the penetration through the tissues is concerned.

Under the same experimental conditions, the indomethacin, the phenylbutazone and the acetylsalicyclic acid, on the other hand, prove to be completely devoid of local anaesthetic effects.

IRRITATING ACTION

In parallel with the study of the local anaesthetic action, there was studied the local irritating effect which manifests itself with phenomena of edema and reddening respectively in the eye, in the case of the local anaesthesia in the rabbit, and in the tail, in the case of anaesthesia by infiltration in the mouse. The "products" did not cause any local phenomenon of irritation even at doses twice as high as those which possess local anaesthetic effects.

With the benzydamine, on the other hand, there was observed an overlapping between the doses having local anaesthetic effects and those causing irritation.

DISINFECTING ACTION

There was employed the common cup test, on a solid culture ground. The following microorganisms were studied: *Escherichia Coli; Streptococcus Aureus* and *Faecalis; Klebsiella pneumoniae; Pseudomonas aerouginosa; Candida albicans; Aspergillus niger; Saccaromices cerevisiae.*

The "products" have exercized a non-specific antimicrobic action, i.e., of the disinfecting type, beginning at a concentration of 0.05%. The benzydamine has exercized a similar effect, qualitatively and quantitatively. On the other hand, the phenylbutazone, the indomethacin and the acetylsalicylic acid have proven inactive.

ULCEROGENIC ACTION

The "products" have resulted free of ulcerogenic effects up to a dose of 250 mg/kg p.o., when studied in the rat, using the conditions described by Cioli et al. (V. Cioli, B. Silvestrini, F. Dordoni, Exp. mol. Patol., 6, 68, 1967).

The pharmacological data thus indicate that the "products" are pharmaceutical agents which possess mainly anti-inflammatory effects. They clearly differentiate themselves from the so-called aspirin-like agents both because of the absence of ulcerogenic effects on the gastrointestinal mucous membrane and because of their major effectiveness through the oral route.

The 2-benzyl-3-(3-dimethylaminopropylthio)-2H-indazole (I) may be prepared with different syntheses which may be subdivided in four different types.

(A) By alkylation of the known 2-benzyl-indazolin-3-thione (IV) (G. Corsi et al. Annali Chimica, Rome, 60, 246–258, 1970) according to the following scheme:

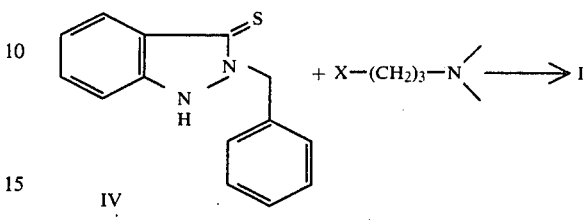

where X is a suitable replaceable group. The nature of X may vary and the choice depends on reason of opportunity, such as availability of the relative substrate, problems of installations and of work safety.

It may be, for example, a halogen (particularly Cl), a sulfonic ester

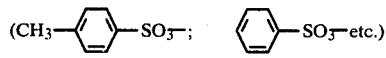

or even a hydroxy group if in the presence of suitable catalysts.

According to replaceable group selected, the reaction conditions will vary.

The 2-benzyl-indazolin-3-thione (IV) may thus be transformed into the corresponding anion while the reaction may be carried out in the most various polar or non-polar organic solvents or in a double phase water-solvent.

The modalities to obtain the anion will be selected in function of the solvent as well as of the availability and handling ease of the base to be utilized. It will thus be possible to suspend an alkaline salt or an alkaline-earth salt of the 2-benzyl-indazolin-3-thione (IV), prepared according to standard techniques, in an organic solvent and adding a solution, in the same or in another solvent compatible with the first, of 3-chloropropyl-N,N-dimethylamine or of another alkylating agent among those described. Alternatively, it will be possible to generate the anion in situ, for example by mixing the two reaction components in a solvent and in the presence of an alkaline carbonate.

The reaction may be carried out in a single phase using a polar solvent such as ethanol. In such case it will be possible to utilize the sodium salt of 2-benzyl-indazolin-3-thione or to salify it in loco by adding it to an equimolar solution of an alkyline ethylate.

Finally it is also possible to treat an aqueous solution of the sodium salt of 2-benzyl-indazolin-3-thione (IV) with a solution, in a suitable organic solvent, of the alkylating agent in the presence of a phase transfer agent.

Furthermore, it is not always necessary to transform the 2-benzyl-indazolin-3-thione (IV) into the corresponding anion.

In the particular case in which X=Cl, if it is desired to obtain the hydrochloride of the 2-benzyl-3-(3-dimethylaminopropylthio)-2H-indazole (I), it is possible to react the 2-benzyl-indazolin-3-thione (IV) as such directly with the 3-chloropropyl-N,N-dimethylamine in a suitable organic solvent at a temperature which will generally be the reflux temperature of the solvent itself. If the solvent chosen is a nonpolar solvent, the I-hydrochloride will separate directly as such during the reaction, while if the solvent is polar said hydrochloride will generally crystallize on cooling the solution at the end of the reaction.

Also then in the case in which there is utilized as replaceable group the OH group the reaction may be carried out on the non-salified thiol and in the presence of suitable catalysts. As catalyst there can be successfully used the dicyclohexylcarbodiimide and a small quantity of cuprous chloride.

As will result clear to those skilled in the art, other reaction conditions, such as time and temperature, may be selected from case to case in function of the particular reaction chosen and of the installations available for realizing same.

The maximum temperatures utilizable will be, however, those of the boiling point of the solvents, at atmospheric pressure, while it will not be necessary to come down to temperatures lower than the ambient temperature.

The reaction time, for reason of convenience, will vary between few minutes (for reactions carried out at high temperatures and in continuous apparatus) and up to a maximum of 18 hours, in the most unfavorable cases.

(B) Alternatively, the 2-benzyl-3-(3-dimethylaminopropylthio)-2H-indazole (I) may be obtained by the action of the known 3-dimethylaminopropylthio on a 2-benzyl-3-halo-indazole (V) according to the following scheme:

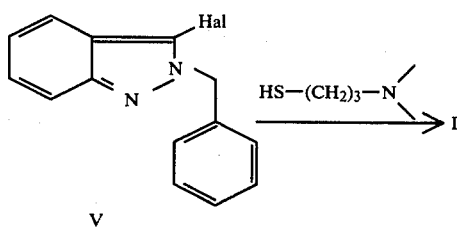

V

As in the reactions of type A, also in this case the reaction conditions, solvent, temperature, time will vary in function of the particular technique selected and it will generally be suitable to act on the anion of the 3-dimethylaminopropylthiol.

The 2-benzyl-3-chloro-indazole has been described in the literature while the 3-bromo may be prepared by standard methods starting from the known 2-benzyl-1,2-dihydro-3H-indazol-3-one.

(C) A third type of synthesis of the 2-benzyl-3-(3-dimethylaminopropylthio)-2H-indazole (I) is described by the following scheme:

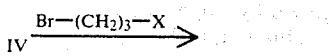

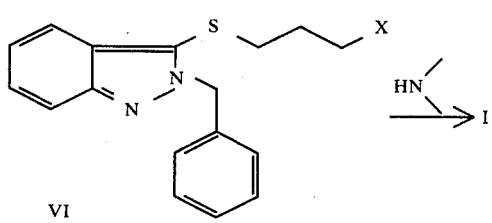

VI

Also in this case X can be halogen, or a sulfonic ester derivative or may also be OH.

In the particular case in which X=Cl there will be used as intermediate the 2-benzyl-3-(3-chloropropylthio)-indazole (VI$_a$) which is easily available.

The 2-benzyl-indazolin-3-thione (IV) reacts in fact easily with 1-bromo-3-chloropropane in the presence of a base suitable to salify it, both in polar and non-polar solvents, to give the 2-benzyl-3-(3-chloropropylthio)-indazole (VI$_a$) in good yields.

For X=OH, the 2-benzyl-3-(3-hydroxypropylthio)-indazole is prepared by the action of the 3-chloropropanol on the sodium salt of (IV). The alcohol thus obtained (VI$_b$) can then be transformed into the sulfonyl derivative by conventional techniques.

Compound (VI) (X=halogen or a sulfonic ester) reacts with solutions of dimethylamine in both polar and non-polar solvents to give (I) as the hydrochloride.

The use of gaseous dimethylamine is obviously possible but in general, unless special installations are used, it is less advantageous as will become clear to one skilled in the art.

When then, in (VI), X=OH, the reaction with dimethylamine will require the use of a catalyst, such as the dicyclohexylcarbodiimide already mentioned for the synthesis of type A.

This same type of synthesis is applicable for the preparation of the sulfoxide (II) and of the sulfone (III) corresponding to (I). In fact (VI) may be oxidized with peracids to the corresponding sulfoxide or sulfone (VII and VIII) according to the peracid used and the reaction conditions selected. By action of the dimethylamine in conditions similar to that described for the preparation of (I), from (VII) and (VIII) there can then be obtained (II) and (III):

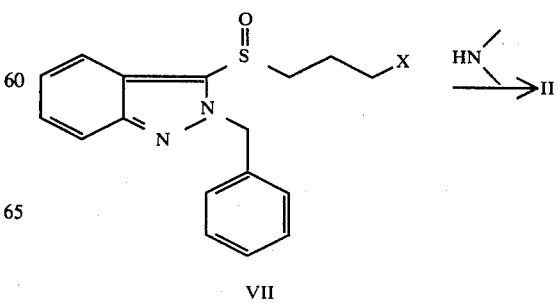

VII

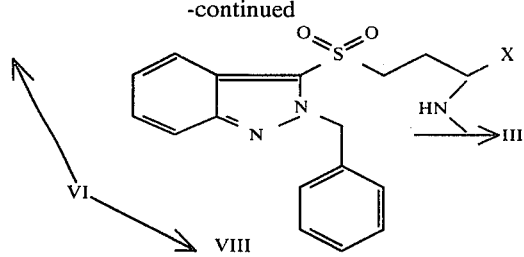

(D) The 2-benzyl-3-(3-dimethylaminopropylthio)-2H-indazole (I) may finally be obtained by the reduction of the amide (IX) with a suitable reducing agent such as, for example, lithium aluminum hydride:

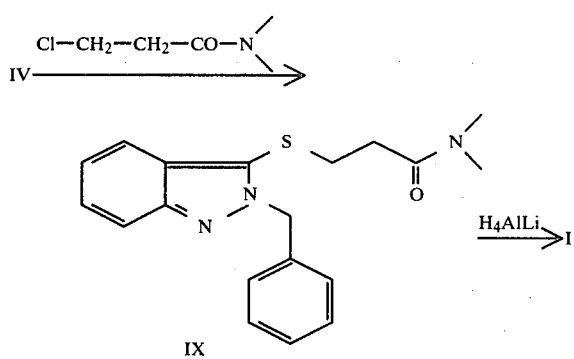

The amide (IX) is in turn prepared by the action of the known 3-chloro-N,N-dimethyl-propanamide on the anion of the 2-benzyl-indazolin-3-thione (IV) in both polar and non-polar solvents.

The compounds (I), (II) and (III) may be used in therapy both in the form of bases and in the form of salts with pharmacologically compatible acids. The experts in the art know these salts which may be inorganic (such as hydrochloride sulfate, phosphate, nitrate, etc.) or organic (maleate, citrate, tartrate, etc.).

On the basis of the pharmacological informations, the "products" find a therapeutic use in one of the suitable pharmaceutical forms well known to those skilled in the art; the pharmaceutical formulation will vary in accordance with the various indications.

Thus, for systemic administration, in the common inflammatory diseases, one or more of these "products" will be used in the form of tablets, in doses between 10 and 100 mg, 3 times a day, or as vials, suppositories or any other form which can be administered through the oral, parental or rectal route.

For topical administration, there is foreseen a differentiated use, for example, with one or more of the following pharmaceutical forms:

(a) mouth wash (0.05–0.20%) in the inflammatory diseases of the oral cavity;

(b) ointment (1–5%) in the inflammatory forms of the articulation and of the muscular and skeletal apparatus in general;

(c) gynaecological wash (0.05–2%) in the inflammatory diseases of the external genital apparatus and of the vagina;

(d) proctological cream (0.5–2%) in proctitis and haemorrhoidal infections; or with any other form suitable for the particular use and known to those skilled in the art.

The following non-limiting examples illustrate the invention:

EXAMPLE 1

In a solution of 3.3 g of sodium (0.14 mols) in 350 ml of methanol there are dissolved 34.5 g (0.14 mols) of 2-benzylindalozin-3-thione.

When the solution is complete, the methanol is evaporated completely under reduced pressure and on a steam bath. The dry sodium salt thus obtained is suspended in 370 ml of toluene containing 21.7 g (0.17 mols) of 3-chloropropyl-N,N-dimethylamine. The mixture is allowed to boil with vigorous stirring for 5 hours. The mixture is then cooled, the organic phase is washed with water and the solvent is evaporated. The residue (45.6 g) is a slightly yellowish oil which is dissolved in anhydrous ether. To the resulting solution there is added an equimolar quantity of anhydrous hydrogen chloride in ethereal solution.

The hydrochloride thus obtained is collected by filtration and recrystallized from isopropanol.

Yield: 44.5 g (87.8%): m.p. 152°–153° C.

U.V. Spectrum: $\lambda max = 304$ nm, $\epsilon = 8,800$

By freeing the base and salifying it with the respective acids by means of standard techniques it is possible to obtain the citrate, m.p. 98°–101° (dec.); the oxalate, m.p. 177°–179°; the fumarate, m.p. 133°–135°; the maleate, m.p. 114°–116°; the mesylate, m.p. 127°–130°.

EXAMPLE 2

In 10 ml of absolute ethanol there is dissolved 0.095 g (0.0041 mols) of sodium. There are then added, in this order, 1 g (0.0041 mols) of 2-benzyl-indazolin-3-thione and 0.6 g (0.0041 mols) of 3-chloropropyl-N,N-dimethylamine.

The mixture is refluxed for 2 hours and poured in an excess of water. The oil which separates is extracted with hexane. The residue which is obtained by removing the solvent is transformed into the hydrochloride as described in Ex. 1.

Yield: 1 g (70%); m.p. 151°–152°.

EXAMPLE 3

A mixture formed by 10 ml of 2 N NaOH (0.02 mols), 2.4 g (0.01 mols) of 2-benzyl-indazolin-3-thione, 2 g of Aliquat and 15 ml of a xylene solution containing 1.82 g (0.015 mols) of 3-chloropropyl-N,N-dimethylamine is refluxed for 2 hours. The organic phase is separated, throughly washed with water and dried. Anhydrous hydrogen chloride is then added thereto and the hydrochloride which separates is recrystallized from isopropanol.

Yield: 2 g (55.3%); m.p. 150°–152°.

EXAMPLE 4

The sodium salt of the 2-benzyl-indazoline-3-thione (5.26 g, 0.02 mols), prepared according to Ex. 1, is suspended in 50 ml of toluene. There is then added an ether solution of the p-toluenesulfonate of 3-dimethylaminopropanol, containing 6.5 g (0.02 mols) of said compound and 50 ml of ethyl ether and the mixture is refluxed with stirring for 7 hours. At the end of the heating cycle, the reaction mixture is extracted with 50 ml of 2 N HCl, the aqueous phase is separated and made basic with NaOH. The oil which separates is extracted with ethyl ether. The resulting ether solution is then treated directly with an ether solution of anhydrous hydrogen chloride. The resulting chlorohydrate is filtered and recrystallized from ethanol. There is obtained 3.8 g (52.6%) of product; m.p. 152°–153°.

EXAMPLE 5

6 g (0.025 mols) of 2-benzyl-indazolin-3-thione are dissolved in 24.3 ml of a xylene solution containing 12.5% (0.0025 mols) of 3-chloropropyl-N,N-dimethylamine. The mixture is refluxed for 2 hours, cooled and the solvent is removed therefrom by decantation. The gummy residue is taken up with ethyl acetate until, on scratching, crystallization takes place. The solid thus obtained is collected by filtration and recrystallized from isopropanol.

Yield: 5 g (55.5%); m.p. 151°–152°.

EXAMPLE 6

A mixture of 2.5 g (0.012 mols) of dicyclohexylcarbodiimide, 1 g (0.01 mols) of 3-dimethylaminopropanol and 25 mg of CuCl is heated with stirring and under a nitrogen atmosphere for 2 hours at 90°. There is then added a suspension of 2.4 g (0.01 mols) of 2-benzyl-indazolin-3-thione in 10 ml of toluene. The mixture is refluxed for 9 hours and the reaction mixture is then diluted with benzene and extracted with 20 ml of 2 N HCl. The acid extract is made alkaline with NaOH and the oily residue which separates is collected and transformed into the hydrochloride according to the techniques already described in the preceding examples.

There are obtained 2 g (55.3%) of hydrochloride; m.p. 151°–3°.

EXAMPLE 7

A suspension, containing 12 g (0.0049 mols) of 2-benzylindazolin-3-thione and 6.9 g (0.05 mols) of potassium carbonate in 120 ml of xylene, is brought to its boiling point. There is then slowly added, over a period of about 30', 24.3 ml of a 25% solution of 3-chloropropyl-N,N-dimethylamine (0.05 mols) in xylene. After the mixture is allowed to boil for 3 hours, it is cooled and washed with water. The residue which is obtained after removal of the solvent is transformed into the hydrochloride with the technique described in Ex. 1. There is obtained 10 g (55.3%) of product; m.p. 150°–151°.

EXAMPLE 8

To a solution of 0.5 g (0.02 mols) of sodium in 50 ml of absolute ethanol there is added 2.3 g (0.01 mols) of 2-benzyl-3-chloro-indazole and then 1.6 g (0.01 mols) of 3-dimethylaminopropanethiol hydrochloride. The mixture is boiled for 16 hours and then, after cooling, is poured into 100 ml of water. The oil which separates is extracted with ether and the residue, which is obtained after removing the solvent, is transformed into the hydrochloride, as described in Ex. 1.

Yield: 1.4 g (39%); m.p. 150°–153°.

EXAMPLE 9

(a) 2-benzyl-3-(3-chloropropylthio)-indazole 2-benzyl-indazolin-3-thione (44.3 g, 0.185 mols) is dissolved in a solution of 12.9 g (0.230 mols) of KOH in 500 ml of water. When the solution is completed there is added 31.9 g (0.203 mols) of 1-bromo-3-chloropropane. The mixture is heated with stirring on a steam bath for 3 hours and is then cooled. The oil which forms is extracted with ether and the residue which is obtained by removing the solvent (59 g; yield: 100%) results unitary under TLC and its NMR is in accordance with the expected structure.

(b) 2-benzyl-3-(3-dimethylaminopropylthio)-2H-indazole 5.5 g (0.017 mols) of the preceding product are placed in a closed test tube with 15 ml of a toluene solution of dimethylamine (10% concentration; 0.033 mols). The test tube is heated for 6 hours at 140° and is then cooled. The reaction mixture is poured in water and the organic phase is separated. From said phase, as described in Ex. 1, there is precipitated the hydrochloride.

Yield: 4 g (65%); m.p. 150°–153°.

EXAMPLE 10

(a) 2-benzyl-3-(3-hydroxypropylthio)-indazole

To a solution of 0.92 g (0.04 mols) of sodium in 100 ml of absolute ethanol there is added 9.6 g (0.04 mols) of 2-benzyl-indazolin-3-thione. The ethanol is removed on a steam bath under reduced pressure and the dry sodium salt thus obtained is suspended in 50 ml of 3-chloropropanol. The mixture is heated for 3 hours with stirring in a bath kept at a temperature of 180°. At the end of the heating cycle the mixture is poured in water and extracted with ether. The ether extract is dried and the solvent is removed under high vacuum while it is heated in an oil bath at 130° to eliminate also the excess portion of 3-chloropropanol which had been extracted with the ether.

The oily residue is purified by chromatography on a silica gel column, using as the eluent ethyl acetate.

The resulting oil (7.3 g—yield: 61%), which tends to decompose if distillation thereof is attempted, shows by elemental analysis and under NMR spectrum to consist of practically pure 2-benzyl-3-(3-hydroxypropylthio)-indazole. (b) To a solution of 3 g (0.01 mols) of the preceding product in 15 ml of pyridine there is added 1.9 g (0.01 mols) of p-toluenesulfonylchloride. The mixture is left for 3 hours under stirring at room temperature, is then poured into 100 ml of a water-ice mixture and the oil which separates is extracted with ethyl ether. The oil which is obtained by removing the solvent is dissolved in 20 ml of a toluene solution containing 10% (0.044 mols) of dimethylamine and the resulting solution is heated for 16 hours at 120° in a closed test tube. At the end of the heating cycle, the toluene solution is extracted with an equal volume of 2 N HCl and made basic with NaOH. The oil which separates is extracted with ether and to the ether solution there is added gaseous HCl. The hydrochloride which precipitates is removed by filtration and recrystallized from isopropanol-isopropyl ether.

Yield: 2 g (55%); m.p. 149°–152°.

EXAMPLE 11

In a Pyrex tube of suitable dimensions are placed 2.5 g (0.012 mols) of dicyclohexylcarbodiimide, 2.98 g (0.01 mols) of 2-benzyl-3-(3-hydroxypropylthio)-indazole and 25 mg of CuCl.

The mixture is heated under nitrogen for 2 hours at 120°. There is added 20 ml of a solution of 10% dimethylamine (0.044 mols) in toluene. The tube is flame-sealed and is heated for 9 hours at 130°. At the end of the heating cycle the tube is opened and the reaction mixture is diluted with toluene and extracted with 2 N HCl. The acid solution is made basic and the oil which separates is extracted with ether. The residue which is obtained when the solvent is removed is dissolved in anhydrous ether and transformed to the hydrochloride as described in Ex. 1.

Yield: 1.8 g (49.5%); m.p. 151°-153°.

EXAMPLE 12

7.6 g (0.06 mols) of 3-chloro-propionyl chloride are added dropwise, with stirring, into 60 ml of a 10% solution of dimethylamine (0.12 mols) in toluene while cooling with an ice-water mixture. After stirring for 1 hour, while continuously cooling the mixture with ice and water, the solution is filtered (solution A).

To a suspension of 13.15 g (0.05 mols) of the sodium salt of 2-benzyl-indazolin-3-thione, prepared according to Ex. 1, in 100 ml of toluene, brought to the boiling point, there is added dropwise, over a period of one half hour, the solution A. The mixture is refluxed for 5.5 additional hours and is then cooled and washed with water. After removal of the solvent, the residue (16.6 g; yield: 89%) shows an NMR spectrum which is in good accordance with the structure (IX).

4.5 g (0.01 mols) of the preceding product are dissolved in 20 ml of anhydrous ether. This solution is added dropwise, with stirring, while cooling with water and ice, to a suspension of 0.4 g (0.01 mols) of $LiAlH_4$ in 40 ml of anhydrous ether. At the end of the addition, the mixture is refluxed for 4 hours. The excess of hydride is decomposed with the usual techniques and the hydrochloride precipitates directly from the resulting ether solution.

Yield: 3.2 g (88.5%); m.p. 151°-152°.

EXAMPLE 13

2-benzyl-3-(3-dimethylaminopropylthio)-2H-indazole sulfoxide 16.2 g (0.051 mols) of 2-benzyl-3-(3-chloro-propylthio)indazole are dissolved in 100 ml of chloroform; to this solution, after cooling, are added gradually over 20' 120 ml of a 0.5 M perbenzoic acid solution in chloroform. After 2 hours of stirring at room temperature, the resulting solution is washed with 10% sodium carbonate and then with water. After removal of the solvent, the residue, after recrystallization from hexane-ethyl acetate, shows a melting point of 76°-78°.

Yield: 14 g (82.3%).

10.1 g (0.032 mols) of the preceding product are heated in a closed tube at 120° for 4 hours with 100 ml of a 5% (0.11 mols) dimethylamine solution in toluene. At the end of the heating cycle, the toluene solution is washed with water and then extracted with 100 ml of N HCl. The aqueous phase is separated and made basic with NaOH; the oil which separates is extracted with ether and the solvent is evaporated. The residue (7.5 g) is dissolved in absolute ethanol and to the solution is added 2.68 g of maleic acid. The maleate, recrystallized from ethyl acetate-absolute ethanol, shows a melting point of 147°-149°.

Yield: 6 g (42.5%).

EXAMPLE 14

Sulfone of the 2-benzyl-3-(3-dimethylamino-propylthio)-2H-indazole 16.2 g (0.051 mols) of 2-benzyl-3-(3-chloropropyl-thio)indazole are dissolved in 60 ml of acetic acid. To the solution is added 20 ml of hydrogen peroxide (30% concentration) and the solution is heated for 3 hours on a steam bath. At the end of the heating cycle, the mixture is poured in water and the oil which separates is extracted with ethyl ether. The ether solution is washed with water and bicarbonate and the solvent is then evaporated. The residue, after recrystallization from hexane-ethyl acetate, shows a melting point of 91°-93°.

Yield: 16.2 g (90%).

11 g (0.032 mols) of the preceding product are heated in a closed tube with 110 ml of a 5% (0.12 mols) dimethylamine solution in toluene. After 6 hours at 160°, the reaction mixture is poured in water, the oil which separates is extracted with ether and is then re-extracted from the ether solution with hydrochloric acid. The oil which is obtained when the aqueous phase is made basic is again taken up in ether. This new solution is dried, the solvent is removed and the residue (10 g) is transformed into the hydrochloride with an alcoholic solution of anhydrous hydrogen chloride. The hydrochloride recrystallized from ethyl acetate-ethanol, shows a melting point of 151°-153°.

Yield: 7.4 g (56.4%).

The corresponding free base, recrystallized from hexane, shows a melting point of 58°-60°.

What is claimed is:

1. A compound for use in treatment of inflammatory conditions selected from the group consisting of 2-benzyl-3-(3-dimethylaminopropylthio)-2H-indazole (I), its sulfoxide (II) and its sulfone (III) and their pharmaceutically acceptable acid addition salts:

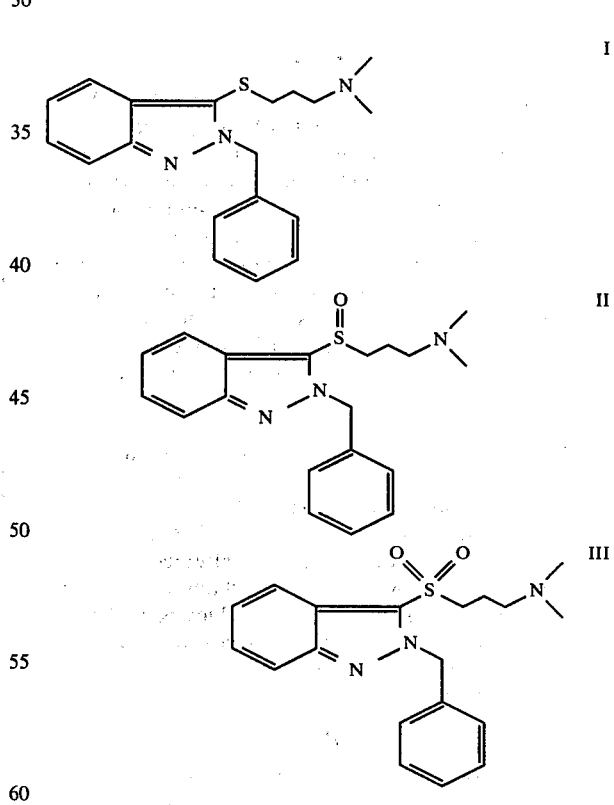

2. The compound of claim 1, which is 2-benzyl-3-(3-dimethylaminopropylthio)-2H-indazole (I) or its pharmaceutically acceptable acid addition salts.

3. The compound of claim 1, which is the sulfoxide of the 2-benzyl-3-(3-dimethylaminopropyl-thio)-2H-indazole (II) or its pharmaceutically acceptable acid addition salts.

4. The sulfone of the 2-benzyl-3-(3-dimethylaminopropylthio)-2H-indazole (III) or its pharmaceutically acceptable acid addition salts.

5. A method for treating the common pathological conditions of the inflammatory type which consists in the administration of an anti-inflammatory amount of one or more of the compounds selected from the group consisting of formulae (I), (II), (III) in accordance with claim 1 and their pharmaceutically acceptable acid addition salts.

6. A method for treating the common pathological conditions of the inflammatory type according to claim 5 in which said administration takes place by the systemic route.

7. A method for treating the common pathological conditions of the inflammatory type according to claim 5 in which said administration takes place by the topical route.

8. A pharmaceutical composition for use in the treatment of inflammatory conditions, which comprises as a therapeutically active component an anti-inflammatory amount of at least one of the 2-benzyl-3-substituted-2H-indazole compounds and their pharmaceutically acceptable acid addition salts as claimed in claim 1.

* * * * *